US010722674B2

(12) United States Patent
Nashed (10) Patent No.: US 10,722,674 B2
(45) Date of Patent: *Jul. 28, 2020

(54) RESPIRATORY FACE MASK AND BREATHING CIRCUIT ASSEMBLY

(71) Applicant: Ramses Nashed, Tierra Verde, FL (US)

(72) Inventor: Ramses Nashed, Tierra Verde, FL (US)

(73) Assignee: Sedation Systems, LLC, Clearwater, FL (US)

( * ) Notice: Subject to any disclaimer, the term of this patent is extended or adjusted under 35 U.S.C. 154(b) by 776 days.

This patent is subject to a terminal disclaimer.

(21) Appl. No.: 15/342,256

(22) Filed: Nov. 3, 2016

(65) Prior Publication Data

US 2017/0072156 A1    Mar. 16, 2017

Related U.S. Application Data

(63) Continuation of application No. 14/479,843, filed on Sep. 8, 2014, now abandoned, which is a continuation
(Continued)

(51) Int. Cl.
*A61M 16/08* (2006.01)
*A61M 16/06* (2006.01)
(Continued)

(52) U.S. Cl.
CPC ...... *A61M 16/0891* (2014.02); *A61M 16/009* (2013.01); *A61M 16/0009* (2014.02);
(Continued)

(58) Field of Classification Search
CPC .............. A61M 16/00; A61M 16/0009; A61M 16/0078; A61M 16/009; A61M 16/01;
(Continued)

(56) References Cited

U.S. PATENT DOCUMENTS 3,556,097 A    1/1971 Wallace
3,856,051 A  * 12/1974 Bain ................... A61M 16/009
                                                    138/114
(Continued)

FOREIGN PATENT DOCUMENTS

AD    2162757 GB    2/1986
WO     9700092 A1    1/1997

OTHER PUBLICATIONS

Zier et al., Case-Series of Nurse-Administered Nitrous Oxide for Urinary Catheterization in Children, Anesthesia & Analgesia, Apr. 2007, vol. 104, No. 4, pp. 876-879.
(Continued)

*Primary Examiner* — Annette Dixon
(74) *Attorney, Agent, or Firm* — Smith & Hopen, P.A.; Steven M. Forte (57) ABSTRACT

A disposable breathing circuit is adapted to be connected between a disposable face mask and a vacuum source for delivering fresh gas to the face mask and for scavenging waste gas exhaled from the face mask. The breathing circuit includes a fresh gas supply limb and an exhalation limb, and a scavenging limb coupled to the exhalation limb. The scavenging limb includes a one-way valve to prevent re-breathing, a flexible flow-through reservoir bag used to store exhaled gas, and an output tube adapted to be coupled between the flow-through reservoir bag and the vacuum source.

20 Claims, 6 Drawing Sheets

Related U.S. Application Data of application No. 12/658,019, filed on Feb. 1, 2010, now Pat. No. 8,826,905, which is a continuation-in-part of application No. 12/455,048, filed on May 28, 2009, now abandoned, which is a continuation-in-part of application No. 12/221,379, filed on Aug. 1, 2008, now Pat. No. 8,826,909, which is a continuation-in-part of application No. 11/809,435, filed on Jun. 1, 2007, now Pat. No. 8,336,549.

(51) Int. Cl.
*A61M 16/00* (2006.01)
*A61M 16/10* (2006.01)
*A61M 16/01* (2006.01)

(52) U.S. Cl.
CPC ........ *A61M 16/0078* (2013.01); *A61M 16/01* (2013.01); *A61M 16/06* (2013.01); *A61M 16/0683* (2013.01); *A61M 16/085* (2014.02); *A61M 16/0816* (2013.01); *A61M 16/0833* (2014.02); *A61M 16/0875* (2013.01); *A61M 16/104* (2013.01); *A61M 16/1015* (2014.02); A61M 2202/0208 (2013.01); A61M 2202/0283 (2013.01); A61M 2230/432 (2013.01)

(58) Field of Classification Search
CPC .. A61M 16/06; A61M 16/0683; A61M 16/08; A61M 16/0816; A61M 16/0833; A61M 16/085; A61M 16/0875; A61M 16/0891; A61M 16/1015; A61M 16/104; A61M 16/107; A61M 2202/0208; A61M 2202/0283; A61M 2205/7518; A61M 2230/432; F16L 11/20; F16L 11/22; Y10S 128/26; Y10S 128/912
See application file for complete search history.

(56) References Cited

U.S. PATENT DOCUMENTS

| | | | |
|---|---|---|---|
| 3,960,148 A | 6/1976 | Dryden | |
| 4,112,940 A | 9/1978 | Parkes | |
| 4,248,218 A | 2/1981 | Fischer | |
| 4,265,239 A | 5/1981 | Fischer, Jr. | |
| 4,312,339 A | 1/1982 | Thompson, Sr. | |
| 4,520,808 A | 6/1985 | LaBauve | |
| 4,527,558 A | 7/1985 | Hoenig | |
| 4,850,350 A * | 7/1989 | Jackson | A61M 1/0043 128/207.16 |
| 5,404,873 A * | 4/1995 | Leagre | A61M 16/08 128/203.29 |
| 5,485,835 A | 1/1996 | Vande Streek et al. | |
| 5,676,133 A | 10/1997 | Hickle et al. | |
| 6,273,087 B1 * | 8/2001 | Boussignac | A61M 16/12 128/200.12 |
| 6,578,571 B1 | 6/2003 | Watt | |
| 6,948,493 B2 | 9/2005 | Dunlop | |
| 7,849,853 B2 | 12/2010 | Grychowski et al. | |
| 7,900,633 B2 | 3/2011 | Sinha | |
| 8,333,198 B2 | 12/2012 | Sinha | |
| 8,336,549 B2 | 12/2012 | Nashed | |
| 8,550,076 B2 * | 10/2013 | Nashed | A61M 16/009 128/200.24 |
| 8,726,900 B1 | 5/2014 | Nashed | |
| 8,826,905 B2 * | 9/2014 | Nashed | A61M 16/0078 128/203.28 |
| 8,826,909 B2 | 9/2014 | Nashed | |
| 2002/0148464 A1 * | 10/2002 | Hoenig | A61M 16/08 128/200.24 |
| 2005/0103346 A1 | 5/2005 | Noble | |
| 2006/0032509 A1 | 2/2006 | Milles | |
| 2008/0251082 A1 | 10/2008 | Sinha | |
| 2009/0044807 A1 * | 2/2009 | Boussignac | A61M 16/04 128/205.25 |
| 2009/0235932 A1 | 9/2009 | Nashed | |

OTHER PUBLICATIONS

International Search Report and Written Opinion for PCT/US2011/000166 (filing date: Jan. 28, 2011) dated Nov. 1, 2011; Applicant: Nashed Ramses.
International Preliminary Report on Patentability for PCT.US2011/000166 (filing date: Jan. 28, 2011) with a priority date of Feb. 1, 2010; Applicant: Nashed Ramses.
Further Examination Report for New Zealand IP No. 601551 dated Aug. 4, 2014; Applicant: Ramses Nashed.
Examination Report for New Zealand IP No. 601551 dated Apr. 26, 2013; Applicant: Ramses Nashed.
Extended Search Report for European Application No. 11737410.8-1662/2531248 (PCT/US2011000166) dated Nov. 19, 2014; Applicant: Nashed, Ramses.
European Communication pursuant to Article 94(3) EPC for European Application No. 11737410.8-1662 dated Oct. 21, 2015; Applicant: Nashed, Ramses.
European Communication pursuant to Article 94(3) EPC for European Application No. 11737410.8-1662 dated Sep. 8, 2016; Applicant: Nashed, Ramses.

* cited by examiner

RESPIRATORY FACE MASK AND BREATHING CIRCUIT ASSEMBLY

BACKGROUND OF THE INVENTION

1. Field of the Invention

The present application relates generally to devices for delivering respiratory gas or gases in medical applications, and more particularly, to a new and improved respiratory face mask and breathing circuit assembly that is especially useful in administering gases, such as anesthesia inhalation agents, or oxygen, or air, or mixtures of same, for medical purposes, and as such represents an improvement over the similar device or devices disclosed in my prior applications.

2. Brief Description of the Related Art

In my prior applications, I fully disclose a disposable anesthesia face mask assembly having a flexible hollow inflatable sealing cushion extending along substantially the entire peripheral edge of the face mask shell or body member to prevent anesthesia gas or the like delivered through the gas portal on the face mask from escaping and adversely affecting the surgical environment. The unique face mask assembly disclosed in my prior applications represents a significant advance over the prior art because, inter alia, it is the only respiratory or anesthesia face mask now known having a pneumatic sealing cushion that extends over and under the chin portion of the patient's face and surprisingly, as a result of this unique arrangement, requires only a relatively simple single headstrap or band for maintaining the face mask in a stable position even during long duration surgical procedures. Hence, the face mask and headstrap assembly of my prior applications are ideally suited for use during so-called "sedation" anesthesia procedures where the patient breathes on its own.

A well-known safe and effective sedation anesthetic in gas inhalation form is nitrous oxide ($N_2O$). This compound, frequently called "laughing gas" or "happy gas," has been used medically for many years usually as an analgesic or "light sedative" to ease pain associated with trauma, childbirth or heart attacks, for example, or as a carrier for more potent anesthesia gases (e.g. Desflurane, Sevoflurane). Indeed, nitrous oxide is so safe, easy to handle, and readily available relatively inexpensively, it has been used as an anesthetic in dentistry since the 1800s. When used by a dentist, nitrous oxide is typically administered through a demand-valve or continuous inhaler placed over the patient's nose so that the patient's mouth can be worked on while the patient continues to inhale the gas. A full facemask, therefore, cannot be used in dentistry, and to avoid build-up of exhaled or waste nitrous oxide, which can pose an intoxicating and prolonged-exposure hazard to the clinic staff in the room where the procedure is being conducted, a continuous-flow-fresh-air ventilation system or nitrous-scavenging system must be used.

In "Case Series of Nurse-Administered Nitrous Oxide for Urinary 10 Catheterization in Children," Anesthesia & Analgesia 2007, 104:876-879, Judith L. Zier, M D. et al, the authors reported the use of $N_2O$ to "sedate" children undergoing a painful procedure in a hospital setting. Administration of the nitrous was carried out using commercially available "dental" equipment to supply the $N_2O$ gas and to scavenge exhaled waste (through a nose mask). Thus, the authors reported that a "comfortable seal could be maintained . . . over the nose of the older child" (emphasis added). Nitrous oxide is only minimally metabolized in the human body. Accordingly, unless provision is made to collect or otherwise scavenge the breath of a patient exhaled through the mouth, build-up of exhaled $N_2O$ waste gas in the hospital environment using such "dental equipment" cannot reasonably be avoided. In order to overcome the foregoing disadvantages, the present application discloses a new and improved respiratory face mask and breathing circuit assembly adapted to be used with commercially available nitrous oxide gas handling equipment used in dentistry. When so employed, the disposable respiratory face mask and breathing circuit assembly of the present invention completely avoids contaminating the surrounding environment with built-up waste $N_2O$ gas thereby facilitating safe and effective combined use of such equipment for sedation purposes in a hospital or other clinical environment. An enclosed environment is not exposed to exhalation gas received from said disposable respiratory face mask because a novel breathing circuit is disposed in fluid communication between said disposable respiratory face mask, a gas delivery device, and a vacuum source.

BRIEF SUMMARY OF THE INVENTION

The present invention, briefly described, provides a uniquely combined anesthesia face mask and breathing circuit adapted to be sealing coupled to a conventional "dental" nitrous gas set-up having a fresh-gas-supply module and a vacuum or scavenging module. The breathing circuit includes at one end thereof a cylindrical hollow plug or nozzle for insertion within the main gas flow passage of the face mask. A fresh-gas, flexible supply tube also is joined to the breathing circuit nozzle and is adapted to be coupled at its opposed distal other end to the outlet nozzle on the fresh gas supply module of the "dental" set-up. At the other or opposed end of the breathing circuit, a collapsible, flexible flow-through gas reservoir bag is suitably provided. The reservoir bag's distal end is joined to one end of a gas flow compensator which, in turn, suitably is adapted to be coupled at its other opposed end to the vacuum module of the "dental" set-up. When so arranged, the face mask and breathing circuit of the present invention permits fresh gas supplied from the "dental" set-up to be sealingly inhaled continuously by a patient being "sedated" and any and all exhaled waste gas whether expelled through the patient's nose or mouth is safely scavenged via the face mask and the breathing circuit by the vacuum module of the "dental" setup thereby avoiding re-breathing of exhaled gas by the patient and any build-up of waste $N_2O$ gas in the surrounding environment.

In an alternatively preferred embodiment, the fresh gas supply tube and the exhalation limb of the breathing circuit are replaced by a single length of co-axial flexible tubing connected at one end to the breathing circuit nozzle adapted to be inserted into the face mask main port and at its other opposed end to a branched coupling. The branched coupling, in turn, includes a first branch for connection to the fresh gas supply nozzle of the "dental" set-up and a second branch for connection to a flexible flow-through reservoir bag. A one-way valve is disposed between the second branch output nozzle and the input of the flexible bag. The output of the flexible flow-through bag is connected to the vacuum module of the "dental" set-up. The second branch of the coupling; the one-way valve, and the flexible flow-through reservoir bag define the exhalation limb of the breathing circuit. Fresh gas is drawn through the first branch coupling, the flexible co-axial tubing and flows into the mask to be inhaled by a patient whereas any exhaled or waste gas flows back through the flexible co-axial tubing, the second branch coupling, the one-way valve, the flexible flow-through reservoir bag and ultimately to the vacuum module of the "dental" set up.

There has thus been described, rather broadly, several important features of the invention in order that the detailed description thereof that follows may 20 be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved respiratory face mask and breathing circuit assembly which has all of the advantages of the prior art and none of the disadvantages.

It is another object of the present invention to provide a new and improved face mask and breathing circuit that is especially suitable for use in administering anesthesia inhalation gas or gases to a patient continuously without causing any exhaled waste gas to build-up in the surrounding area.

It is a further object of the present invention to provide a new and improved face mask and breathing circuit assembly which is of durable and reliable constructions.

An even further object of the present invention is to provide a new and improved respiratory face mask and breathing circuit assembly which is susceptible of a low cost of manufacture with regard to both materials and labor, and which accordingly is then susceptible of low prices of sale, thereby making such a face mask and breathing circuit assembly economically available to the medical community.

Even still another object of the present invention is to provide a new and improved respiratory face mask and breathing circuit assembly that may be used on a patient before, during or after surgery in a safe and efficient manner.

It is yet another object of the present invention to provide a new and improved respiratory face mask and breathing circuit assembly where the breathing circuit is adapted to be coupled to the fresh gas supply module of a nitrous oxide "dental set" and further includes means for connecting the breathing circuit to the vacuum module of the same "dental set."

Still yet another object of the present invention is to provide a new and improved respiratory face mask and breathing circuit assembly where the breathing circuit is adapted to be coupled to the fresh gas supply module of a nitrous oxide "dental set" and further includes means for automatically preventing re-breathing of waste gas exhaled into said breathing circuit.

Yet still yet another object of the present invention is to provide a new and improved respiratory face mask and breathing circuit assembly where the breathing circuit is adapted to be coupled to the fresh gas supply module of a nitrous oxide "dental set" and further includes an exhalation limb for storing waste gas exhaled into the breathing circuit by the patient and for avoiding rebreathing of any of the waste gas by the patient.

Another object of the present invention is to provide a new and improved respiratory face mask characterized by at least two primary components, namely a cup-like shell or receptacle member terminating at its peripheral edge in a peripheral flange, and an annular substantially donut-shaped hollow inflatable cushion or sealing member affixed or otherwise permanently attached to the flange along substantially the flange's entire peripheral extent, in combination with a breathing circuit adapted to be coupled between the cup-like shell member and a device for supplying anesthesia gas normally used in dentistry.

Even still yet another object of the present invention is to provide a disposable anesthesia face mask and breathing circuit assembly ideally suited for use during "sedation" anesthesia procedures where the patient is self-breathing.

It is still yet another object of the present invention to provide a breathing circuit including a length of co-axial flexible tubing connected to a branched coupling which in turn includes a first branch for connection to a fresh gas supply nozzle of a "dental" set-up and a second branch for connection through a one-way valve to a flexible flow-through reservoir bag used to store waste or exhaled gas.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DETAILED DESCRIPTION OF THE PREFERRED EMBODIMENT

With reference initially to FIGS. 1-4 of the Drawings, there is shown a preferred embodiment of the new and improved respiratory face mask and breathing circuit assembly of the present invention generally comprising a face mask 10, a breathing circuit 12, and a gas supply and scavenging device 14.

Figure 1:
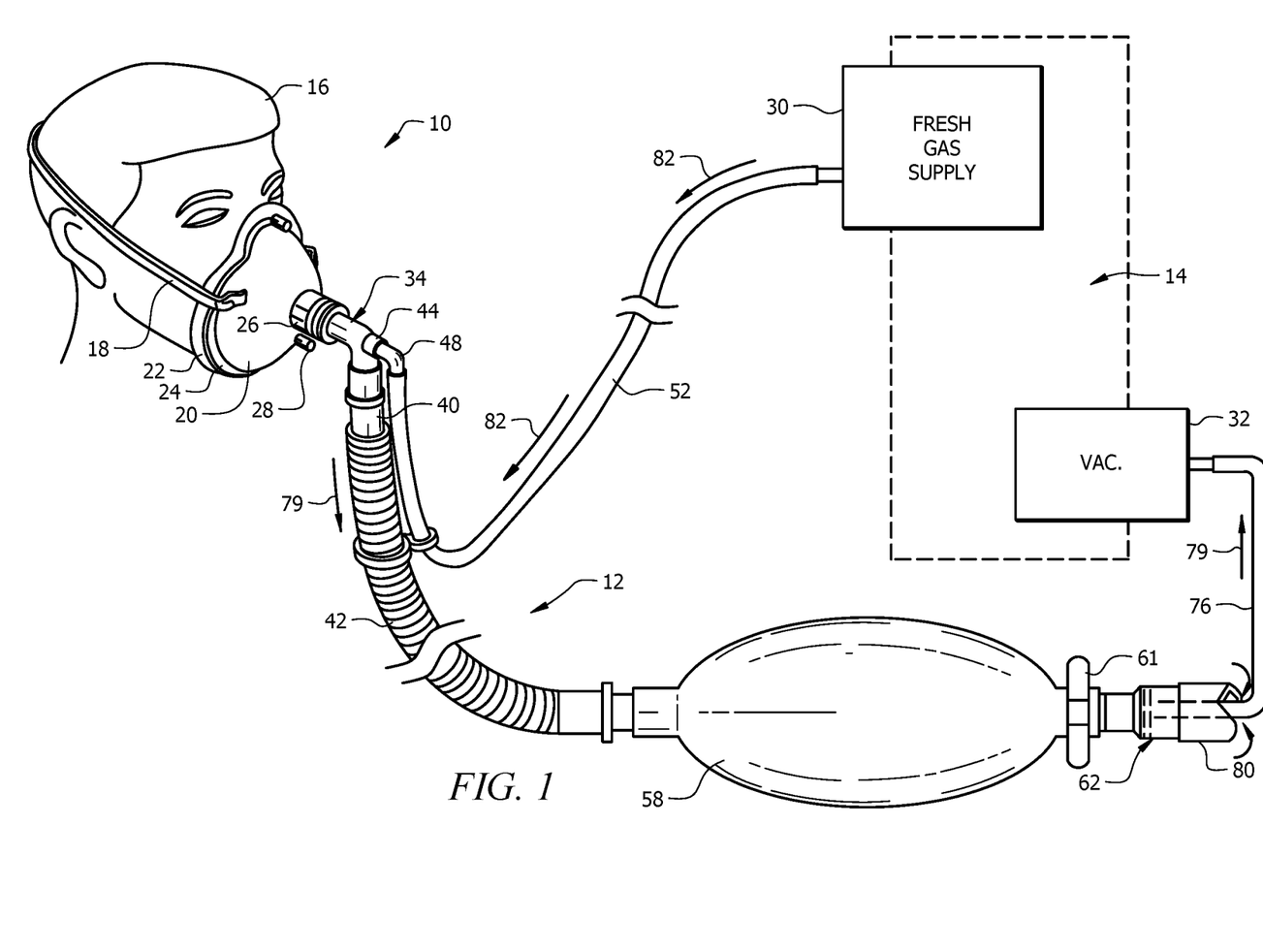
FIG. 1 is a schematic perspective view of the respiratory face mask and breathing circuit assembly of the present invention where the face mask is depicted fitted to a patient and is connected to the fresh gas supply module and vacuum module, respectively, of an anesthesia gas supply and scavenging device.

As schematically depicted in FIG. 1, face mask 10 is fitted on the face of a patient 16 via a headstrap 18 (preferably elastic) removably attachable to the face mask via anchors or the like on the opposed edges thereof. The headstrap helps to stabilize the face mask on the face and head of a person, preferably before, during and/or after surgery. Many of the details of construction of the face mask 10 and headstrap 18 are outside the scope of the present invention. For a more detailed understanding of same, the interested reader is directed to my prior applications (incorporated herein by reference). Suffice it to say for purposes of fully understanding the present invention, face mask 10 preferably is similar to that fully disclosed in my prior applications and therefore, comprises a cup-like shell or receptacle member 20 and a flexible pneumatic cushion member 22. The flexible pneumatic cushion member 22 defines a generally donut-shaped sealing member extending annually along the entire extent of a peripheral rim or flange 24 defined by the shell member 20.

As further disclosed in my prior applications, the crown portion of shell member 20 has a cylindrical hollow inlet member or cylindrical port 26 suitably sized to removably receive in snug sliding (and sealing) engagement therein the nipple of a conventional breathing circuit and to define a passageway such that anesthesia gas or other gases are adapted to pass from a source through the breathing circuit and the passageway into the interior of shell member 20. The breathing circuit also is adapted to receive returned or exhaust gas or gases through the same passageway and convey such exhausted gas or gases to a conventional gas evacuation or scavenging apparatus such as is provided on a standard anesthesia machine used in surgery rooms. Shell member 20 also may include a second cylindrical hollow outlet member or port 28 for connection to a length of flexible tube (not shown) the other or distal end of which is adapted suitably to be connected to a conventional $CO_2$ monitoring device or capnograph for sensing end-tidal $CO_2$ of a breathing patient.

As further disclosed in my prior applications, when the face mask 10 is applied to the face of a patient, the top portion of the face mask receives and covers the nose portion of the patient, the intermediate portion of face mask covers the mouth portion of the patient, and the bottom or widest portion of the face mask receives and engages the underside of the chin and jaw portion of the patient's face with the pneumatic cushion member 22 effectively serving to seal the periphery of the face mask relative to the patient's face and preventing escape of anesthesia gas or other gas into the surrounding environment notwithstanding the irregular contour of the patient's face. As further disclosed in my prior applications, the foregoing engagement between the underside of the chin or jaw portion of the patient with the bottom or widest transverse edge portion of the face mask prevents displacement of the face mask toward the ocular area, helps to keep the patient's mouth closed, and securely stabilizes the face mask assembly on the face when the elastic headstrap is used thereby freeing both hands of attending anesthesia personnel for use elsewhere. It will be appreciated in connection with carrying out the present invention, that the face mask 10, depicted in FIG. 1, can be fitted to the face and head of a patient in the foregoing manner, or in the manner described in my prior applications.

In accordance with the present invention, and as schematically depicted in FIG. 1, a uniquely modified breathing circuit 12 is employed to deliver anesthesia gases or the like originating from gas supply and scavenging device 14 to face mask 10. Device 14 is of the well-known type commonly used in the practice of dentistry and comprises inter alia a gas supply module 30 and vacuum module 32 for scavenging waste gas or exhaled gas. By way of example, such devices are commercially available from Porter Instrument, Hatfield, Pa. 19440 and now are in widespread use. Thus, as is well known, the gas supply module 30 in such "dental" devices is adapted to supply both nitrous oxide and oxygen and has valve controls for adjusting the flow of each to produce a mixture of any desired concentration. The vacuum module 32 provides a source of negative pressure (vacuum) and can be wall-mounted to provide a convenient outlet. It will be understood that the constructional details of these devices are conventional and outside the scope of the present invention.

Modified breathing circuit 12 includes a Y-connector 34 having a first tubular plug or nipple 36 suitably sized for mating engagement within the first cylindrical inlet member or cylindrical port 26 on face mask 10. Y-connector 34 also features a second tubular branch or nipple 38 for mating with a first open cylindrical end 40 of flexible corrugated tubing 42 and a third tubular branch or receptacle 44 for mating with a first tubular end or nipple 46 of elbow connector 48. The second or opposed end 50 of elbow connector 48 is adapted to be connected to a supply tube 52 which in turn is connected to the output of the gas supply module 30 of "dental" gas supply and scavenging device 14 (FIG. 1).

Flexible corrugated tubing 42 terminates in a second open end 54 which in turn is adapted to be matingly engaged with the first cylindrical open end 56 of flexible collapsible reservoir bag 58. The opposed second cylindrical end of reservoir bag 58 terminates in a cylindrical plug 60 having a rotatable gate valve therein (not shown) controlled by handle 61. Rotation of handle 61 in either direction about the central longitudinal axis of the plug 60 varies the size of a suitable opening provided in the distal end of plug 60 between a minimum and a maximum extent, respectively. The purpose of the gate valve is to adjust the flow of exhaled waste gas through the reservoir bag 58 somewhat if desired as will be made more evident below.

Thus far breathing circuit 12 is similar to a prior art Modified Jackson Rees (MJR) breathing circuit used in General Anesthesia applications. In order to adapt breathing circuit 12 for purposes of the present invention, the cylindrical plug 60 located on the second end of reservoir bag 58 is operatively coupled to a gas flow compensator 62 the purpose of which is to automatically assure that any waste gas exhaled into the breathing circuit will not be rebreathed by the patient, or escape into the surrounding environment, but rather will safely be evacuated via the vacuum module 32 of gas supply and scavenging device 14. Gas flow compensator 62 generally is tubular in shape and has a first end defining a cylindrical receptacle 64 for receivingly mating with plug 60. The opposed second end of compensator 62 defines a cylindrical opening 66 exposed to the surrounding environment.

Alternatively, gas flow compensator 62 may advantageously be integrated with plug 60 to form a one-piece or unitary construction. In such a case, the gate valve and its handle 61 is obviated and maybe may dispensed with if desired.

Figure 2:
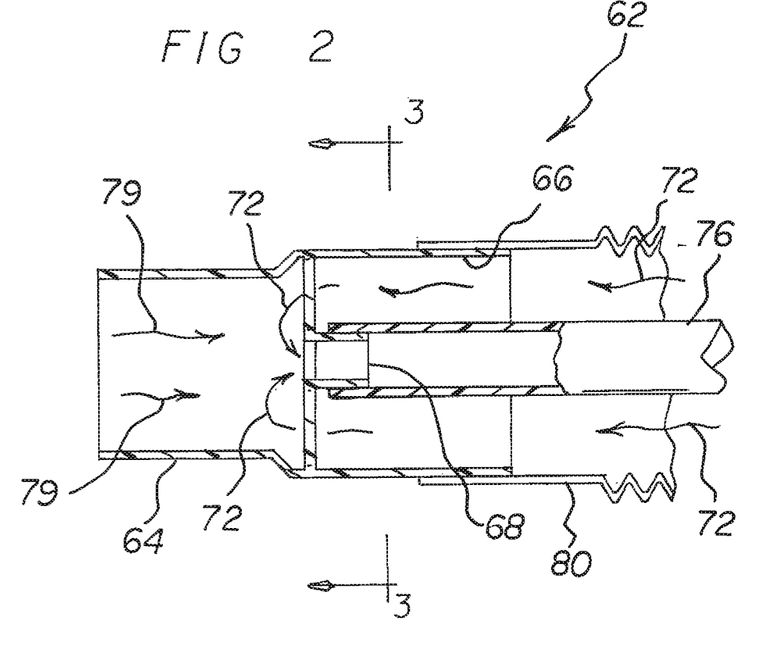
FIG. 2 is an enlarged cross-sectional view in elevation of a portion of the respiratory face mask and breathing circuit assembly of FIG. 1 taken along line 2-2 of FIG. 3 (i.e. element 62).
Figure 3:
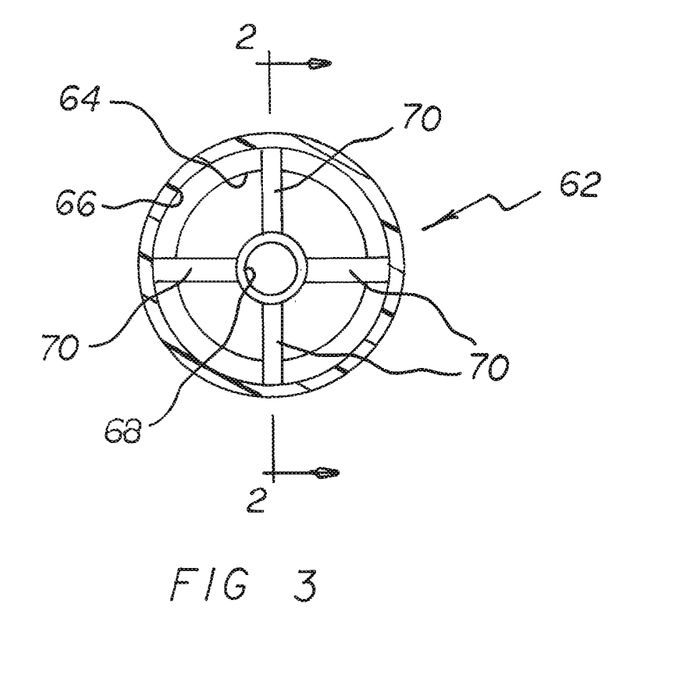
FIG. 3 is a cross-sectional view taken along line 3-3 in FIG. 2.
Figure 4:
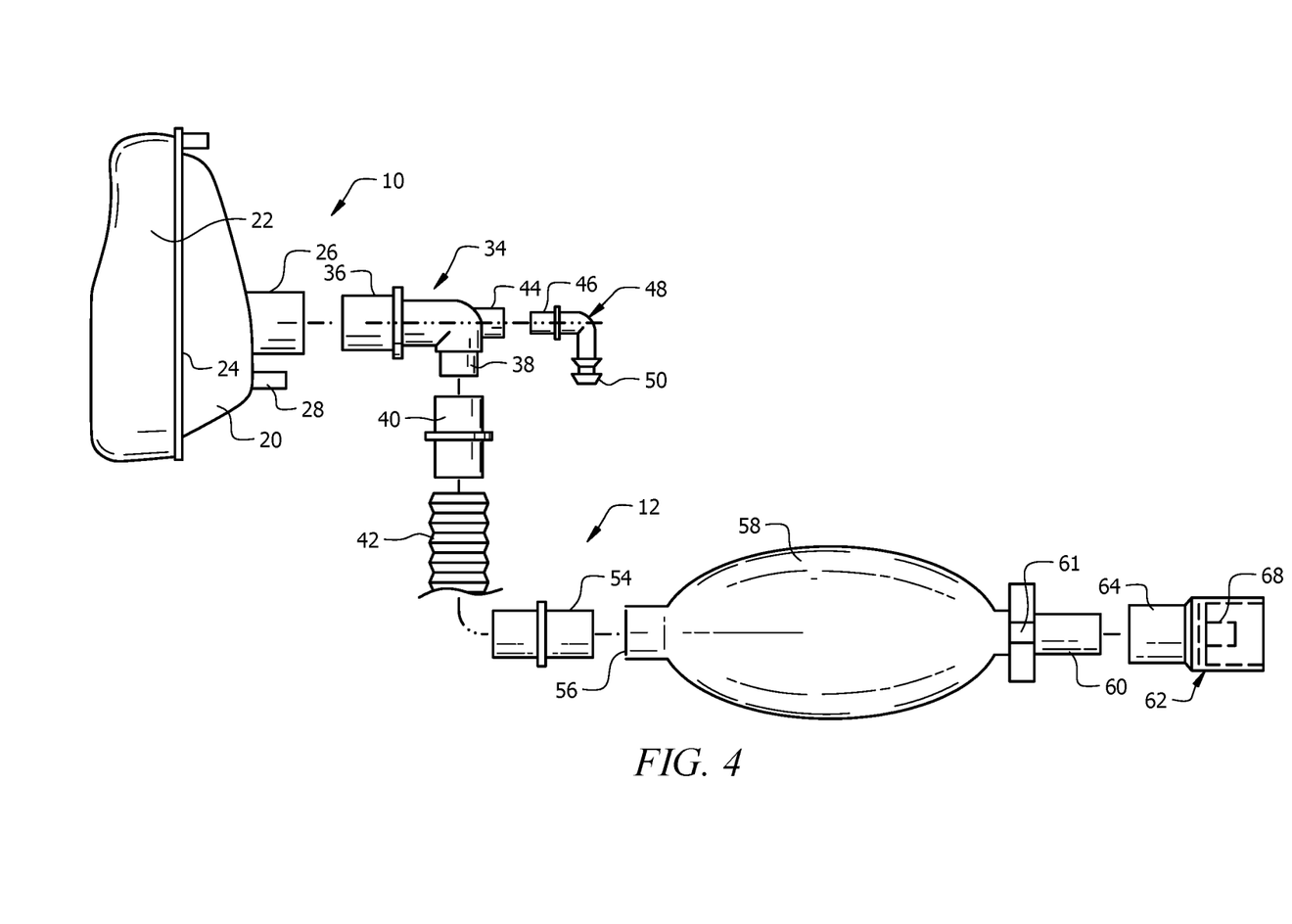
FIG. 4 is an assembly view of the various parts making up the respiratory face mask and breathing circuit assembly of the present invention.

Mounted interiorly of compensator 62 substantially medially of the first and second opposed ends thereof and coaxially therewith is a nozzle 68 of reduced diameter relative to both cylindrical receptacle 64 and cylindrical opening 66 substantially as shown in FIGS. 2 and 3. Nozzle 68 preferably is supported at its leftmost end (FIGS. 2 and 3) by a series of four radial struts 70 which serve as a spider suspending the nozzle in its coaxial orientation, but which allow a quantity of air from the environment to pass through cylindrical opening 66 from the right to the left, thence through the openings in the spider as indicated by arrows 72, before entering nozzle 68 through the latter's leftmost open side as viewed in FIG. 2. A length of flexible tubing 76 is suitably securely affixed to nozzle 68 (FIG. 2) proximal to struts 70 and extends coaxially therefrom out through cylindrical opening 66 of the compensator 62 ultimately being connected at its other opposed distal end to vacuum module 32 of "dental" device 14. It will be noted that the length or axial extent of nozzle 68 is not critical, and it suffices if this part has an axial extent or length sufficient to provide a firm gripping surface for the end of flexible tubing 76 attached thereto.

By the foregoing arrangement of parts, it will be appreciated that any exhaled waste gas entering cylindrical receptacle 64 from reservoir bag 58 (arrows 79, FIG. 2) as well as a quantity of outside air entering compensator 62 (arrows 72) will be drawn by the vacuum in flexible tubing 76 through the left side of nozzle 68 and scavenged by vacuum module 32 of device 14. Compensator 62 thus automatically compensates for any dead space in the breathing circuit which might cause exhaled waste gas in the reservoir bag 58 or in the flexible corrugated tubing 42 to stagnate therein and be re-breathed by a patient. Because the face mask 10 has a sealing cushion, leakage of any gas whatsoever into the surrounding environment also is avoided.

Optionally, a cylindrical extension sleeve 80 can be attached to the rightmost side of compensator 62 to increase the effective axial extent of the compensator and thereby form a supplemental reservoir for any exhaled waste gas that may travel along a path from reservoir bag 58 through plug 60 and pass beyond the leftmost side of nozzle 68. Further tweaking of the flow of gases through the gas flow compensator 62 may optionally be attempted by adjusting the position of the handle 61 of the gate valve on the plug 60, but generally, this valve should be placed in the fully "open" position during operation of the disclosed apparatus. Here too, if desired, extension sleeve 80 and the rightmost end of compensator 62 may be formed of a unitary one-piece construction.

In using the apparatus of the invention, and as schematically shown in FIG. 1, it will be seen that fresh gas is adapted to be supplied from gas supply module 30 on "dental" device 14 to the patient through supply tube 52, Y-connector 34, and face mask cylindrical port 26 (arrow 82). Waste or exhaled gas flows into flexible corrugated tubing 42 and reservoir bag 58 under the influence of the vacuum module 32 applying a negative pressure in flexible tubing 76 (arrows 79). All that is necessary after fitting face mask 10 to the face of a patient is to flush (expand) the reservoir bag 58 with a fresh supply of gas from gas supply module 30 of device 14 through supply tube 52 (using the "oxygen flush" button on the fresh gas supply module), attach the breathing circuit Y-connector 34 to the face mask inlet, and connect the flexible tubing 76 from the gas flow compensator 62 to the outlet of vacuum module 32. The patient then will breathe easily through face mask 10 and in so doing draw fresh gas from flexible corrugated tubing 42 and the flushed reservoir bag 58, collapsing the bag. When the patient exhales, the waste gas will fill the bag (and flexible corrugated tubing 42) and be immediately drawn through the gas flow compensator 62 via the negative pressure afforded by flexible tubing 76. At the same time, the negative pressure in flexible tubing 76 will cause fresh gas from supply tube 52 to fill flexible corrugated tubing 42 and reservoir bag 58 so as the patient breathes again, the patient avoids re-breathing any waste or exhaled gas.

Turning now to FIGS. 5-8, there is shown an alternatively preferred embodiment of the face mask and breathing circuit assembly in accordance with the present invention wherein like reference numerals represent like parts already described. In the alternatively preferred embodiment of FIGS. 5-8, as in the prior embodiment, face mask 10 is adapted to be coupled or otherwise connected through a suitable breathing circuit 90 to a "dental" set-up supplying a mixture of nitrous oxide and oxygen and having a scavenging or vacuum module. As schematically depicted, the "dental" set-up, represented generally by reference sign 100, can be an MXR Flowmeter commercially made available by the aforementioned Porter Instrument, Hatfield, Pa. 19440. Typically, this device is mounted on a post supported by a wheeled dolly to render the entire unit portable, or the device may be more permanently mounted on a wall surface via a pivotal bracket or the like. Additionally, it will be appreciated that the Flowmeter device is located proximal to a supply of fresh inhalation gas or gases such as nitrous oxide and oxygen, for example, and to a source of vacuum, which sources may be made available through a conveniently located wall outlet, and coupled to the Flowmeter 100 via suitable flexible hoses or tubing, all as is well known in the art of such "dental" devices.

Flowmeter 100 includes a flowmeter console 102 having valve controls 104, 106 for oxygen ($O_2$) and nitrous oxide ($N_2O$), respectively, which when suitably manipulated can produce an output flow of a desired selected mixture of these two gases through an output nozzle 108. As is well known, Flowmeter 100 suitably is adapted to be connected to a source of nitrous oxide and a source of oxygen as schematically indicated by arrows 110 and 112, respectively. Output nozzle 108, in turn, suitably is connected to an automatic vacuum switch (AVS) module 114 having a fresh (mixed) gas output nozzle 116, a mask-to-vacuum input nipple 118 and vacuum-to-source output nozzle 120. Mask-to-vacuum input nipple 118 is adapted to be connected to the distal end of the exhalation limb of breathing circuit 90 as will be explained in more detail below whereas nozzle 120 is adapted to be connected to a conventional source of "always-on" vacuum as schematically indicated by arrow 122 preferably via a suitable flexible hose or tube and vacuum wall outlet (not shown). It will be noted that the AVS module 114 includes a safety switch that operates to automatically cut-off the vacuum into the module if the flow of mixed gas (e.g. nitrous/oxygen) through the module is interrupted for any reason during operation of the Flowmeter 100.

Figure 6:
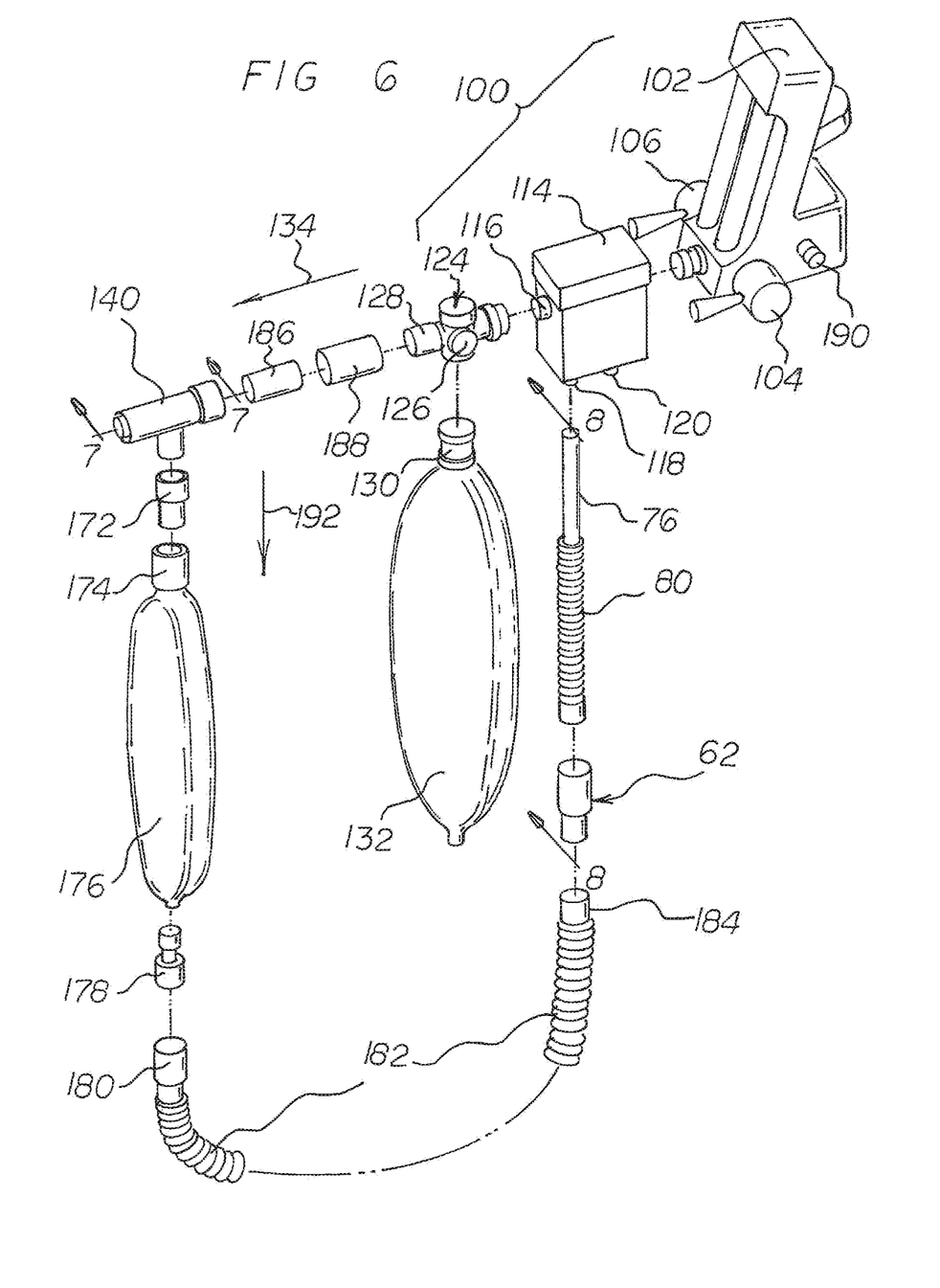
FIG. 6 is an exploded view in perspective of a portion of the alternative preferred embodiment and of the components of the "dental" set-up depicted in FIG. 5.

Output nozzle 116 of AVS module 114 suitably is connected to "Bag Tee" coupling 124 which includes an internal passage (not shown) extending between output nozzle 116 and a first output nozzle 126 on the "Bag Tee" coupling. First output nozzle 126, in turn, is connected to the cylindrical input collar 130 of closed-end flexible reservoir bag 132. The "Bag Tee" coupling 124 further includes a second internal passage (not shown) connected between input collar 130 and a second output nozzle 128 (FIG. 6). By this arrangement, any flow of gas (or gas mixture) from nozzle 116 will enter flexible reservoir bag 132 before exiting the "Bag Tee" through second output nozzle 128. Additionally, a uni-directional demand valve (not shown) suitably is included inside of second output nozzle 128 such that any fresh gas (or gas mixture) stored inside flexible reservoir bag 132 is adapted to flow in the direction of arrow 134 when a patient wearing the face mask and breathing circuit of the present invention inhales as will be discussed in greater detail below.

Flowmeter console 102, AVS module 114, Bag Tee coupling 124 and flexible reservoir bag 132 are part and parcel of a conventional "dental" set-up (e.g. MXR Flowmeter) in widespread use for delivering nitrous oxide to a patient in a dentist's chair through a nose mask and therefore the specific details of construction of these components are well known and understood, forming no part of the present invention. When so employed, patients invariably exhale unmetabolized nitrous oxide into the environment by exhaling through their mouth making the use of such equipment unsuitable in a hospital or clinic environment for "sedation" or other purposes.

In accordance with the present invention, breathing circuit 90 is provided which overcomes the foregoing disadvantage and permits nitrous oxide or other inhalation gases to be employed in a hospital or clinical setting without any contamination of the environment with exhaled gas or gases. Breathing circuit 90 includes a first length of flexible co-axial tubing 136 adapted to be coupled at a first end thereof to face mask 10. Preferably, for this purpose, the first end of co-axial tubing 136 suitably has connected to it a right-angle tube coupling or elbow coupling 138 adapted to be sealingly and securely slidingly fitted into the cylindrical port 26 of the face mask 10. The tube elbow coupling 138 has a cylindrical interior through-passage and defines a nipple suitably sized to sealingly and slidingly fit into cylindrical port 26 of face mask 10 for coupling the interior of flexible co-axial tubing 136 to the interior of face mask 10.

The opposite or second end of flexible co-axial tubing 136 is adapted to be suitably connected to a T-connector 140. The first length of flexible co-axial tubing 136 preferably is corrugated co-axial tubing which is well known in the art of anesthesia respiratory breathing circuits and which includes an inner corrugated sleeve or tube surrounded by an outer corrugated flexible sleeve or tube, with the inner tube adapted to carry inspired fresh gas and the outer tube adapted to carry exhaled gas to and from a patient usually via a laryngeal intubation device inserted into a patient's throat during surgery. Thus, as best seen in FIG. 7, co-axial tubing 136 includes an outer sleeve 142 and an inner sleeve 144 of reduced diameter relative to outer sleeve 142 suitably supported therein to define a first passage 146 (inhalation) surrounded by a second annular passage 148 (exhalation).

Similarly, T-connector 140 preferably is of co-axial design and includes an outer cylindrical wall 150, an inner cylindrical wall 152 of reduced diameter relative to outer cylindrical wall 150, supported therein to define a third passage 154 (inhalation) surrounded by a fourth annular passage 156 (exhalation). Inner cylindrical wall 152 protrudes somewhat from outer cylindrical wall 150 to define a reduced-diameter plug 158 adapted to be slidingly and sealingly received in the T-connector's first end 160 defined by the inner sleeve 144 of co-axial tube when end 162 of outer cylindrical wall is slidingly and sealingly received in end 164 defined by the outer sleeve 142 of co-axial tubing 136, all as substantially depicted in FIG. 7. As further depicted in FIG. 7, inner cylindrical wall 152 of T-connector 140 opens into an enlarged-diameter receptacle 166 at its opposed second end 168 relative to plug 158, which receptacle 166 is in axial open communication with third passage 154.

Figures 7, 8:
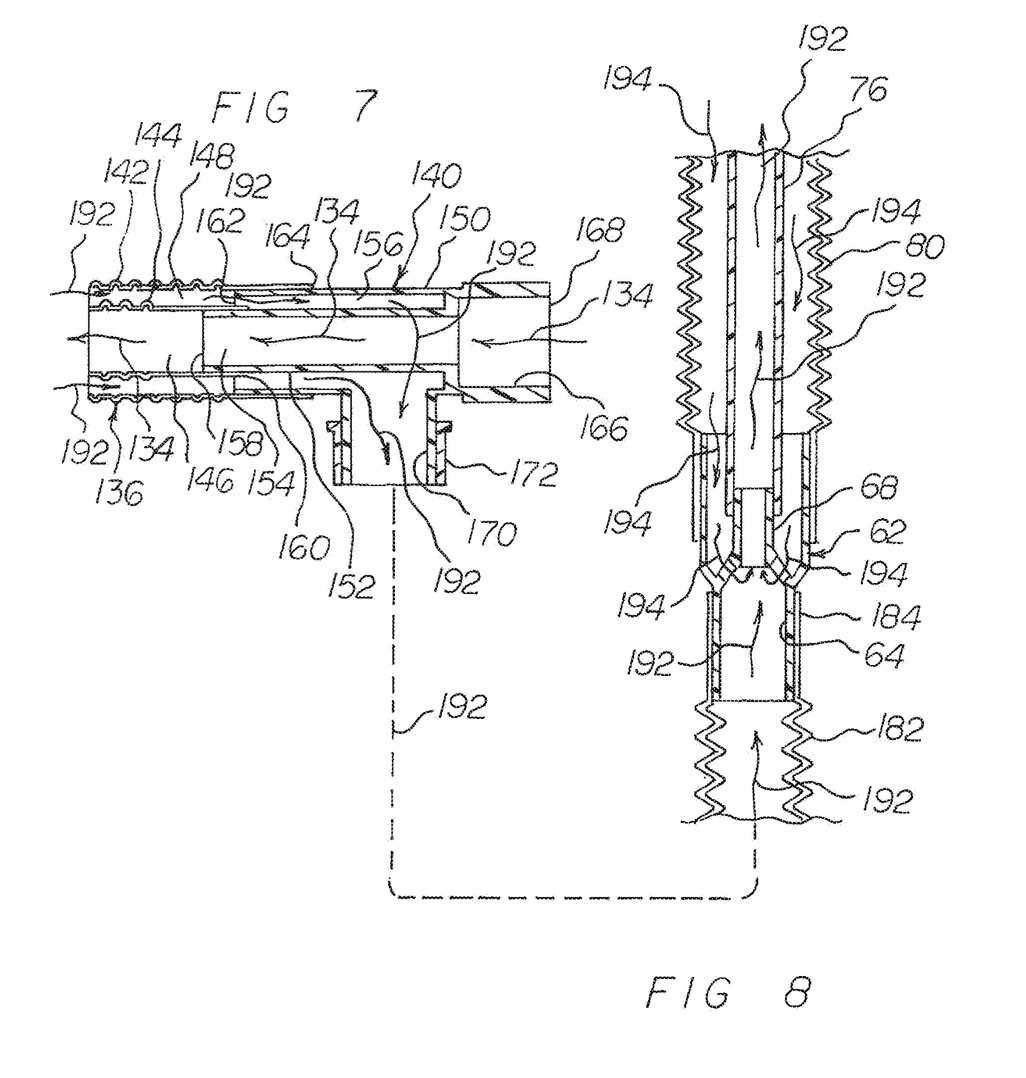
FIG. 7 is a cross-sectional view of T-connector 140 shown in FIGS. 5 and 6 taken along line 7-7 in FIG. 6.
FIG. 8 is a cross-sectional view of the distal portion of the breathing circuit 90 shown in FIGS. 5 and 6 taken along line 8-8 of FIG. 6.

T-connector 140 additionally includes an orthogonally oriented cylindrical output port 170 integral with outer cylindrical wall 150 and extending downwardly therefrom proximal to the juncture of inner cylindrical wall 152 and receptacle 166 as viewed in FIG. 7, which cylindrical output port 170 is in open communication with fourth annular passage 156.

Figure 5:
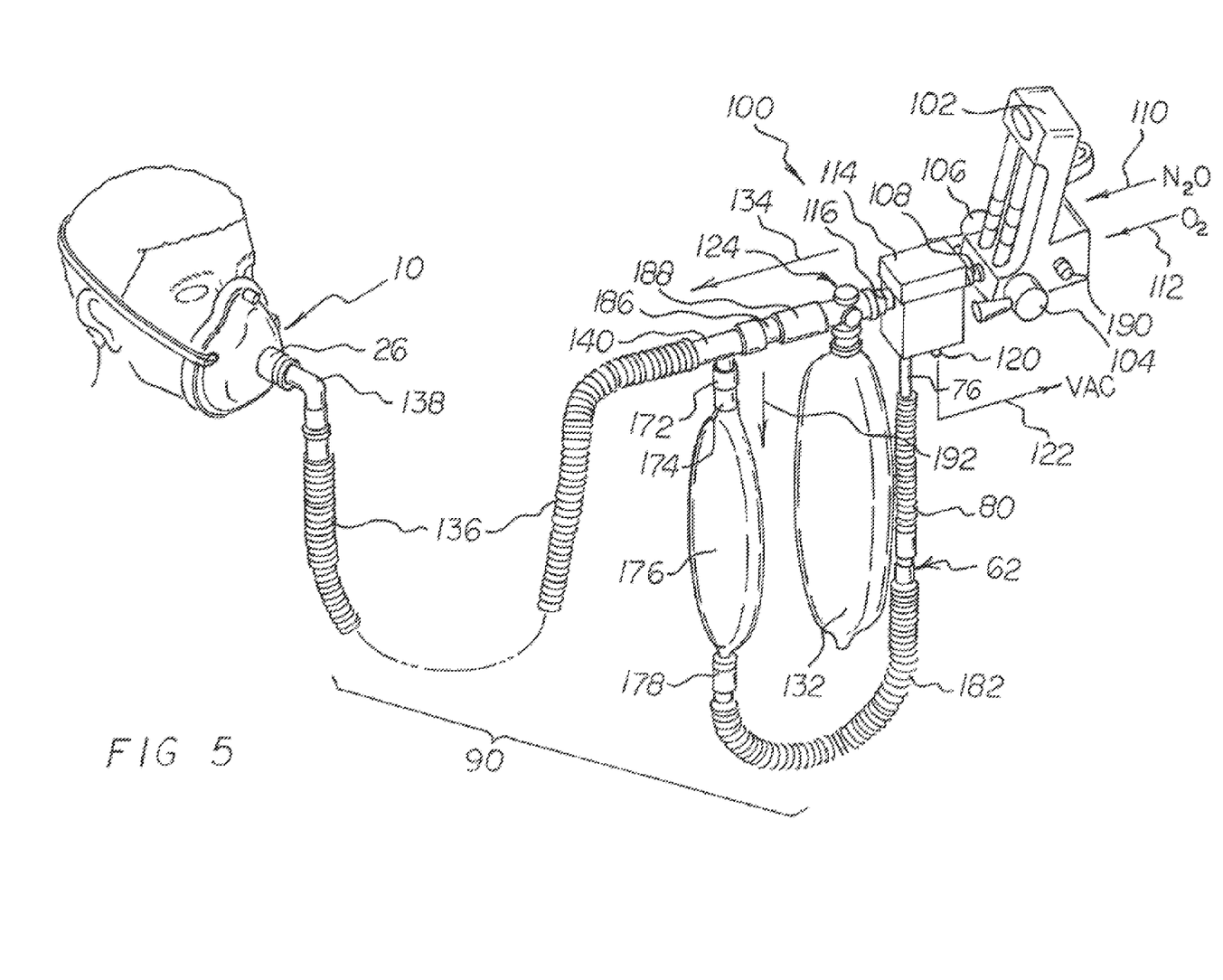
FIG. 5 is a schematic depiction in perspective of an alternatively preferred embodiment of the face mask and breathing assembly according to the invention coupled to a "dental" inhalation gas set-up.

In accordance with the present invention, the cylindrical output port 170 of T-connector 140 is adapted suitably to be slidingly and sealingly received into the cylindrical end portion of a first end of a one-way valve member or housing 172, the opposed other second end of which is adapted suitably to be slidingly and sealingly received within the cylindrical input collar 174 of flow-through flexible reservoir bag 176 (FIGS. 5 and 6). The one-way valve member 172 includes an interior one-way check valve (not shown) for permitting the flow of exhaled gas in one direction, and for preventing or blocking flow of exhaled gas in the opposite direction. Such one-way valve members are well known in the respiratory anesthesia breathing circuit art. For example, the Model No. 1665 one-way valve commercially made available by Teleflex Medical, Durham, N.C. under the designation "Hudson RCI" can be used in breathing circuit 90 as one-way valve member 172 and is mostly preferred.

Flow-through flexible reservoir bag 176 has a first end defined by cylindrical input collar 174 and an open second opposed end suitably and sealingly joined to a cylindrical hollow output bushing 178 which, in turn, is adapted to be slidingly and sealingly received into the hollow cylindrical input collar 180 of a second length of flexible (non-co-axial) tubing 182. Flexible tubing 182 which preferably is corrugated flexible tubing has a hollow cylindrical output cuff 184 adapted to be slidingly sealingly attached to a cylindrical receptacle 64 of gas compensator 62 in the same manner as in my prior embodiment of FIGS. 1-4. Hence, the distal end portion of the breathing circuit 90 can include the gas compensator 62 and the length of flexible tubing 76 suitably securely affixed at one end to nozzle 68 interiorly of compensator 62 and which extends coaxially therefrom out through cylindrical opening 66 of the compensator 62 to ultimately be connected at its other opposed distal to mask-to-vacuum input nipple 118 on the AVS module 114 of dental set-up or Flowmeter 100. In this regard, the optional cylindrical extension sleeve 80 preferably can be attached to the compensator 62 to increase the effective axial extent of the compensator and thereby form a supplemental reservoir for any exhaled waste gas that may travel along a path defined by the second length of tubing 182 and leak from the compensator 62 through the openings surrounding the nozzle 68 and its connection to flexible tubing 76 (FIG. 8).

From the foregoing discussion, it will be appreciated that an important feature of the present invention in its broadest aspect resides in the provision of a length of co-axial flexible tubing connected at one end to a face mask adapted to be sealed on a patient's face, and at its other opposed end to a branched coupling. The branched coupling (T-connector 140), in turn, includes a first branch for connection to the fresh gas supply nozzle of the "dental" set-up and a second branch for connection to a flexible flow-through reservoir bag (bag 176). A one-way valve member 172 is disposed between the second branch output nozzle and the input of the flexible bag. The output of the flexible flow-through bag is connected to the vacuum module of the "dental" set-up. The second branch of the coupling, the one-way valve, and the flexible flow-through reservoir bag define the exhalation limb of the breathing circuit. Fresh gas is drawn through the first branch coupling, the flexible co-axial tubing and flows into the face mask to be inhaled by a patient whereas any exhaled or waste gas flows back through the flexible co-axial tubing, the second branch coupling, the one-way valve, the flexible flow-through reservoir bag and ultimately to the vacuum module of the "dental" set up.

More specifically, with respect to the operation of the alternatively preferred embodiment of FIGS. 5-8, the first end of the flexible co-axial tubing 136 is sealingly connected to face mask 10 by inserting the elbow coupling 138 into cylindrical port 26 of the face mask. Next, the T-connector 140 is sealing and slidingly connected to the first output nozzle 126 of "Bag Tee" 124 of Flowmeter 100 preferably via a pair of suitable co-axial interfitting extension cylindrical tube adapters 186, 188 (FIGS. 5 and 6). The adaptors 186, 188 (which are optional) increase the stand-off distance between T-connector 140 and "Bag Tee" 124 to avoid any possible interference between flexible reservoir bag 176 and flexible reservoir bag 132 during operation. Then, the distal end of breathing circuit 90, namely flexible tube 76 is slidingly and sealing inserted onto mask-to-vacuum input nipple 118 of AVS module 114. When these first three steps are complete, the breathing circuit is sealing coupled to Flowmeter 100 and appears substantially as depicted in FIG. 5.

After assuring the presence of a vacuum on flexible tubing 76, face mask 10 next may be fitted to a patient's face. Before doing so however, it is desirable to cause oxygen to flow through the face mask and this can be accomplished by suitable manipulation of valve controls 104 on Flowmeter console 102 or by pressing the oxygen "flush" button 190 on the Flowmeter console 102 which causes oxygen to flow through the Bag Tee 124 filling reservoir bag 132 with oxygen. Following application of the face mask 10 to a patient's face and after assuring that the face mask is in sealing engagement therewith, control valve 106 may then suitably be manipulated to cause nitrous oxide to flow through the Flowmeter and produce a desired, selected concentration or mixture ratio of nitrous to oxygen, typically up to about 70%, into the flexible reservoir bag 132 through nozzle 116 and ultimately through output nozzle 128 as schematically indicated by arrow 134 (FIGS. 5-6). The foregoing flow of fresh gas (or a mixture of gas) through output nozzle 128 is effective immediately upon inhaling by the patient through sealed-on-the-face mask 10, because this action opens the demand valve in output nozzle 128 releasing the gas or gas mixture stored in flexible reservoir bag 132.

The path of fresh gas when a patient inhales ("inhalation" path) is indicated more graphically in FIG. 7 where arrows 134 represent the flow of the fresh gas entering receptacle 166 at the second end 168 of T-connector 140 from the reservoir bag 132, the output nozzle 128, and the interfitted adaptor tubes 188 and 186; flowing into receptacle 166, then into third passage 154 defined by inner cylindrical wall 152 of T-connector 140, then into first passage 146 defined by the inner sleeve 144 of co-axial tubing 136, and finally through elbow coupling 138 and cylindrical port 26 into the interior of face mask 10.

Upon exhalation by the patient, the exhaled waste gas travels a different path. This different or "exhalation" path is schematically indicated by arrows 192 which represent exhaled waste gas flowing through cylindrical port 26 of face mask 10, elbow coupling 138, second annular passage 148 defined by outer sleeve 142 of co-axial tubing 136, then through fourth annular passage 156 defined by outer cylindrical wall 150 of T-connector 140, the output port 170 of the T-connector 140, one-way valve member 172 and into flow-through flexible reservoir bag 176. In accordance with the present invention, the flexible flow-through reservoir bag 176 is employed in breathing circuit 90 exclusively to store exhaled waste gas. It receives such flow of gas only when the patient exhales through face mask 10 and one-way valve 172 is in an "open" condition. When the patient inhales through face mask 10, one-way valve 172 remains closed and substantially no exhaled gas stored in flexible reservoir bag 176 can be rebreathed by the patient. Rather, during inhalation any waste gas stored in bag 176, is by the action of the vacuum on line 22, evacuated through flow-through bushing 178, the second length of flexible tubing 182, the gas compensator 62, flexible tube 76 mask-to-vacuum input nipple 118, and vacuum-to-source output nozzle 120. It should thus be evident that face mask 10 and breathing circuit 90 provides a completely self-contained system permitting continuous breathing by a patient undergoing "conscious sedation" using nitrous oxide, or a mixture of nitrous dioxide and oxygen, furnished by a "dental" set-up, without contaminating the clinical environment with exhaled waste gas.

In dental set-ups exemplified by the Porter MXR Flowmeter, the vacuum present at mask-to-vacuum input nipple 118 of the AVS module 114 produces a flow rate through this nozzle of about 40 liters/min. Fresh gas flow through the AVS module (output nozzle 116) is on the order of about 10 liters/min. Because of this imbalance, directly connecting the flexible tubing 182 to the mask-to-vacuum input nipple 118 might result in collapsing flexible reservoir bag 176. Gas compensator 62, because it causes room air to be drawn into the evacuation stream as indicated by arrows 194 in FIG. 8, effectively modulates the vacuum source by reducing the vacuum made available at the flow-through bushing 178 at the bottom of bag 176 sufficiently to avoid collapsing flexible bag 176 during operation of breathing circuit 90 due to an excessive vacuum or negative pressure and is another important advantage of the present invention.

The size of flexible bag 132 normally furnished on Flowmeter 100 is about 3 liters. The size of flexible flow-through bag 176 should be large enough to provide ample compliance when a patient exhales through face mask 10 and breathing circuit 90 during normal breathing. A size of about 2 Liters for flexible flow-through bag 176 has been found to provide minimal restriction to exhalation and is particularly preferred.

While the alternatively preferred embodiment of FIGS. 5-8 has been disclosed in connection with the Porter MXR Flowmeter "dental" set-up it will be appreciated that the present invention may be employed with other dental setups for having a nitrous oxide "sedation" capability as well.

Thus, for example, the face mask and breathing circuit assemblies disclosed in this application also may be used with the "Digital Flowmeter" commercially distributed by Accutron Inc., Phoenix, Ariz.

The alternatively preferred face mask and breathing circuit apparatus depicted in FIGS. 5-8 and fully described above with reference to these drawing figures offers many desirable advantages. The use of co-axial flexible tubing between face mask 10 and T-connector 140 provides a more compact and streamlined breathing circuit and helps to avoid snagging and crimping of the fresh gas supply. By arranging the flexible flow-through reservoir bag on the back side of the T-connector 140, the bag is isolated form the co-axial tubing 136 and therefore twisting and crimping of the bag is avoided. The use of a one-way valve member 172 between the T-connector 140 and the flexible reservoir bag 176 assures that little or no waste gas is re-breathed and dispenses with any bleed valve at the bottom or back end of the bag. Still, other advantages will occur to those with ordinary skill in the art.

Finally, it will be appreciated that although the face mask 10 is preferably that disclosed in my prior applications, any known anesthesia face mask having a sealing cushion and sized and configured to fit over the nose and mouth of a patient, such as a standard "General Anesthesia" face mask, may be used in lieu of face mask 10 without departing from the principles of the invention as disclosed above.

From the foregoing description, it should be evident that the apparatus of the present invention solves the vexing problem of providing a suitable "full" face mask and breathing circuit for administering anesthesia gases or other gases employing the relatively portable and inexpensive gas supply and scavenging equipment heretofore used only in the practice of dentistry. By using the face mask and breathing circuit assemblies according to the present invention, in conjunction with such "dental" devices, re-breathing of waste gas by the patient and build-up of waste gas in the clinical room is avoided. As a result, "sedation" anesthesia employing nitrous oxide may now be practiced more readily in hospitals, surgical centers, and doctor's offices in a safe and effective manner thereby leading to increased patient satisfaction and reduced medical costs.

Many variations and modifications to the foregoing will be readily apparent and obvious to one skilled in the art, and all equivalent relationships to those illustrated in the drawings and described in the specification are intended to be encompassed by the present invention. Therefore, it is not desired to limit the invention to the exact construction and operation shown and described, and accordingly, all suitable modifications and equivalents may be resorted to, falling within the scope of the invention as defined in the annexed claims. The face mask and breathing circuit embodiments of the present invention are intended to be disposable and are intended for a single use to avoid cross-contamination. The components of the respiratory face mask and breathing circuit assemblies of the present invention can be made from inexpensive and durable plastic or metal materials. The sealable anesthesia face mask and the breathing circuit embodiments of the invention may be packaged together as a kit or provided in separate packages, respectively.

As to the manner of usage and operation of the instant invention, the same is apparent from the above disclosure, and accordingly, no further discussion relative to the manner of usage and operation need be provided.

What is claimed is:

1. A breathing circuit apparatus for use with a face mask of a patient, a fresh gas output of a gas delivery device, and a vacuum source, said apparatus comprising:
   a main tubular limb, said main tubular limb having opposed first and second ends, said main tubular limb defining a gas supply lumen of first diameter and an exhalation lumen of second diameter disposed with respect to said first diameter lumen along substantially the entire length thereof, said first end of said main tubular limb coupled to said face mask, such that said main tubular limb is in communication with said face mask;
   a branched coupling, said branched coupling having a first connection port, a second connection port, and a third connection port,
   said opposed second end of said main tubular limb being attached to said first connection port of said branched coupling,
   said branched coupling having a first internal passage extending between said first connection port and said second connection port thereof for transmission of said fresh gas output supplied by said gas delivery device to and through said gas supply lumen of said main tubular limb,
   said branched coupling further having a second internal passage extending between said first and third connection ports thereof for receipt and transmission of exhaled patient breath supplied from said face mask through said exhalation lumen of said main tubular limb; and
   a scavenger limb, said scavenger limb having first and second opposed ends, said first end of said scavenger limb being connected to said third connection port of said branched coupling, said second opposed end of said scavenger limb adapted to be releasably connected to said vacuum source,
   wherein said scavenger limb further includes a one-way valve interposed between said first and second opposed ends thereof in proximity to said third connection port of said branched coupling and a gas flow compensator disposed at said second opposed end proximate to said vacuum source, said one-way valve and said gas flow compensator effective to prevent re-breathing of any exhaled patient breath entering said scavenger limb,
   said exhaled waste gas being evacuated from the environment surrounding a patient when said breathing circuit apparatus is disposed in fluid communication between said face mask, said gas delivery device and said vacuum source and said patient breathes through said mask and said breathing circuit.

2. The breathing circuit apparatus of claim 1, further comprising a tubular extension connected to said second branched coupling connection port for releasably connecting said branched coupling to said gas supply output.

3. The breathing circuit apparatus of claim 2, wherein said tubular extension has a first end connected to said branched coupling second port and an opposed second end defining a receptacle, said receptacle being sized to be releasably interference-fitted to said gas supply output.

4. The breathing circuit apparatus of claim 1, wherein said second diameter of said exhalation lumen is larger than said first diameter of said gas supply lumen, such that said gas supply lumen is concentrically positioned within said exhalation lumen.

5. The breathing circuit apparatus of claim 1, wherein said gas supply lumen and said exhalation lumen each is a corrugated co-axial tubing, such that said gas supply lumen is an inner sleeve and said exhalation lumen is an outer sleeve surrounding said inner sleeve.

6. The breathing circuit apparatus of claim 1, wherein said branched coupling includes an outer wall and an inner wall, said inner wall having a smaller diameter than said outer wall, such that a first channel formed within said inner wall defines one of said first internal passage and said second internal passage and a second channel formed between said outer wall and said inner wall defines the other of said first internal passage and said second internal passage.

7. The breathing circuit apparatus of claim 6, wherein said second diameter of said exhalation lumen is larger than said first diameter of said gas supply lumen, such that said gas supply lumen is concentrically positioned within said exhalation lumen, such that said exhaled patient breath follows a path of travel from said exhalation lumen into said second channel of said branched coupling and said fresh gas output follows a path of travel from said first channel of said branched coupling into said inhalation lumen, said second channel in open communication with said third connection port of said branched coupling.

8. The breathing circuit apparatus of claim 1, wherein said scavenger limb includes a flexible reservoir bag coupled to said third connection port of said branched coupling, and wherein said scavenger limb further includes an exhaled air tubing coupled to said flexible reservoir bag and to said vacuum source.

9. The breathing circuit apparatus of claim 8, further comprising:
said scavenging limb further including a scavenging tube, said flexible reservoir bag having an entry opening and an exit opening, said one-way valve being disposed in said scavenging limb between said third connection port of said branched coupling and said entry opening of said flexible reservoir bag such that said entry opening is connected to said third connection port through said one-way valve, permitting unidirectional flow of said exhaled patient breath from said face mask through said third connection port into and through said entry opening, and
said scavenging tube connected to said exit opening for conveying to said vacuum source said exhaled patient breath received in said flexible reservoir bag from said third connection port through said one-way valve.

10. The breathing circuit apparatus of claim 9, further comprising:
a vacuum modulating valve for modulating the vacuum produced by said vacuum source to prevent collapse of said flexible reservoir bag,
said vacuum modulating valve disposed between said exit end of said exhalation bag and said vacuum source in said scavenging tube portion of said scavenging limb.

11. The breathing circuit apparatus of claim 10, further comprising:
said vacuum modulating valve for modulating the vacuum produced by said vacuum source including an outer tube having a first diameter and an inner tube having a second diameter, said first diameter being greater than said second diameter;
at least one opening formed in said vacuum modulating valve enabling ambient air to enter said outer tube and to flow through said inner tube;
said inner tube adapted to be connected to said vacuum source.

12. The breathing circuit apparatus of claim 11, wherein said outer tube of said vacuum modulating valve is connected distally to said scavenging tube, and a supplemental flexible vacuum-connecting tube is connected to said inner tube of second diameter for ultimate connection to said vacuum source.

13. The breathing circuit apparatus of claim 1, wherein said scavenger limb includes an exhaled air tubing coupled on its distal end to said compensator.

14. The breathing circuit apparatus of claim 13, wherein said scavenger limb further includes an extension sleeve coupled to a distal end of said compensator, such that a distal end of said extension sleeve is coupled to said vacuum source, said extension sleeve being a supplemental reservoir for any exhaled patient breath.

15. The breathing circuit apparatus of claim 13, further comprising a concentric nozzle positioned within an interior of said compensator and a plurality of struts disposed around said nozzle to suspend said nozzle in its coaxial orientation, such that external air can pass through said compensator and admix with said exhaled patient breath prior to exiting through said vacuum source.

16. The breathing circuit apparatus of claim 1, further comprising an elbow connector disposed between said face mask and said main tubular limb to facilitate coupling of said face mask and said main tubular limb together.

17. The breathing circuit apparatus of claim 1, wherein said vacuum source is a motorized vacuum source providing a constant vacuum within said scavenger limb.

18. A breathing circuit apparatus for use with a face mask of a patient, a fresh gas output of a gas delivery device, and a vacuum source, said apparatus comprising:
a main tubular limb, said main tubular limb having opposed first and second ends, said main tubular limb defining a gas supply lumen of first diameter and an exhalation lumen of second diameter disposed with respect to said first diameter lumen along substantially the entire length thereof, said first end of said main tubular limb coupled to said face mask, such that said main tubular limb is in communication with said face mask,
wherein said second diameter of said exhalation lumen is larger than said first diameter of said gas supply lumen, such that said gas supply lumen is concentrically positioned within said exhalation lumen,
wherein said gas supply lumen and said exhalation lumen each is a corrugated co-axial tubing, such that said gas supply lumen is an inner sleeve and said exhalation lumen is an outer sleeve surrounding said inner sleeve, such that said exhaled patient breath follows a path of travel from said exhalation lumen into said second channel of said branched coupling and said fresh gas output follows a path of travel from said first channel of said branched coupling into said inhalation lumen, said second channel in open communication with said third connection port of said branched coupling;
an elbow connector disposed between said face mask and said main tubular limb to facilitate coupling of said face mask and said main tubular limb together;
a branched coupling, said branched coupling having a first connection port, a second connection port, and a third connection port,
said opposed second end of said main tubular limb being attached to said first connection port of said branched coupling,
said branched coupling having a first internal passage extending between said first connection port and said second connection port thereof for transmission of said fresh gas output supplied by said gas delivery device to and through said gas supply lumen of said main tubular limb, said branched coupling further having a second internal passage extending between said first and third connection ports thereof for receipt and transmission of exhaled patient breath supplied from said face mask through said exhalation lumen of said main tubular limb, wherein said branched coupling includes an outer wall and an inner wall, said inner wall having a smaller diameter than said outer wall, such that a first channel formed within said inner wall defines one of said first internal passage and said second internal passage and a second channel formed between said outer wall and said inner wall defines the other of said first internal passage and said second internal passage;

a scavenger limb, said scavenger limb having first and second opposed ends, said first end of said scavenger limb being connected to said third connection port of said branched coupling, said second opposed end of said scavenger limb adapted to be releasably connected to said vacuum source, wherein said scavenger limb further includes a one-way valve interposed between said first and second opposed ends thereof in proximity to said third connection port of said branched coupling, said one-way valve effective to prevent re-breathing of any exhaled patient breath entering said scavenger limb, wherein said scavenger limb includes a scavenging tube having an origination end and a terminal end, wherein said origination end is configured to couple to said second opposed end of said scavenger limb and said terminal end is configured to couple to a gas flow compensator, wherein said gas flow compensator is coupled to said vacuum source, such that said gas flow compensator is effective to prevent rebreathing of any exhaled patient breath entering said scavenger limb, a tubular extension connected to said second branched coupling connection port for releasably connecting said branched coupling to said gas supply output, wherein said tubular extension has a first end connected to said branched coupling second port and an opposed second end defining a receptacle, said receptacle being sized to be releasably interference-fitted to said gas supply output, said exhaled waste gas being evacuated from the environment surrounding a patient when said breathing circuit apparatus is disposed in fluid communication between said face mask, said gas delivery device and said vacuum source and said patient breathes through said mask and said breathing circuit.

19. The apparatus of claim 18, wherein said scavenger limb further includes an extension sleeve coupled to a distal end of said scavenging tube, such that a distal end of said extension sleeve is coupled to said vacuum source, said extension sleeve being a supplemental reservoir for any exhaled patient breath.

20. A breathing circuit apparatus for use with a face mask of a patient, a fresh gas output of a gas delivery device, and a vacuum source, said apparatus comprising:
 a main tubular limb, said main tubular limb having opposed first and second ends, said main tubular limb defining a gas supply lumen of first diameter and an exhalation lumen of second diameter disposed with respect to said first diameter lumen along substantially the entire length thereof, said first end of said main tubular limb coupled to said face mask, such that said main tubular limb is in communication with said face mask;

a branched coupling, said branched coupling having a first connection port, a second connection port, and a third connection port, said opposed second end of said main tubular limb being attached to said first connection port of said branched coupling, said branched coupling having a first internal passage extending between said first connection port and said second connection port thereof for transmission of said fresh gas output supplied by said gas delivery device to and through said gas supply lumen of said main tubular limb, said branched coupling further having a second internal passage extending between said first and third connection ports thereof for receipt and transmission of exhaled patient breath supplied from said face mask through said exhalation lumen of said main tubular limb; and a scavenger limb, wherein said scavenger limb includes:
 a first end of said scavenger limb being connected to said third connection port of said branched coupling;
 a second end of said scavenger limb being opposed from said first end, said second end being adapted to be releasably connected to a gas flow compensator in fluid communication with said vacuum source, wherein said gas flow compensator includes a first compensator end defining a receptacle for receiving said second end of said scavenger limb, a second compensator end configured to releasably couple with said vacuum source, and a concentric nozzle positioned within an interior of said compensator and a plurality of struts disposed around said nozzle to suspend said nozzle in its coaxial orientation, such that external air can pass through said compensator and admix with said exhaled patient breath prior to exiting through said vacuum source;
 a one-way valve interposed between said first and second ends of said scavenger limb in proximity to said third connection port of said branched coupling, said one-way valve effective to prevent re-breathing of any exhaled patient breath entering said scavenger limb;
 an exhaled air tubing coupled on its distal end to said compensator;
 an extension sleeve coupled to a distal end of said compensator, such that a distal end of said extension sleeve is coupled to said vacuum source, said extension sleeve being a supplemental reservoir for any exhaled patient breath;
 said exhaled waste gas being evacuated from the environment surrounding a patient when said breathing circuit apparatus is disposed in fluid communication between said face mask, said gas delivery device and said vacuum source and said patient breathes through said mask and said breathing circuit.

\* \* \* \* \*